(12) United States Patent
Lu

(10) Patent No.: US 7,276,035 B2
(45) Date of Patent: Oct. 2, 2007

(54) TEETH CLEANER

(76) Inventor: Sung-Seng Lu, No. 3, Lane 74, Wan-an Rd., Dali City, Taichung County 412 (TW)

(*) Notice: Subject to any disclaimer, the term of this patent is extended or adjusted under 35 U.S.C. 154(b) by 167 days.

(21) Appl. No.: 11/149,245

(22) Filed: Jun. 10, 2005

(65) Prior Publication Data

US 2006/0282027 A1    Dec. 14, 2006

(51) Int. Cl.
*A61H 13/00* (2006.01)
(52) U.S. Cl. .................. 601/162; 601/155; 601/165; 601/169; 433/80
(58) Field of Classification Search ................ 601/154, 601/155, 159, 160–163, 165, 169; 433/80, 433/81–88; 4/615
See application file for complete search history.

(56) References Cited

U.S. PATENT DOCUMENTS

| 3,820,532 | A | * | 6/1974 | Eberhardt et al. | .......... 601/165 |
| 4,043,337 | A | * | 8/1977 | Baugher | ............. 601/162 |
| 4,793,331 | A | * | 12/1988 | Stewart | ............... 601/165 |
| 5,220,914 | A | * | 6/1993 | Thompson | ............ 601/155 |
| 5,934,902 | A | * | 8/1999 | Abahusayn | ............ 601/162 |

* cited by examiner

*Primary Examiner*—Quang D. Thanh
(74) *Attorney, Agent, or Firm*—Troxell Law Office, PLLC

(57) ABSTRACT

An improved teeth cleaner, in which a squirt gun is designed the front end of a handle, and a bending nozzle designed on the foremost position of the squirt gun while its end is designed to be as a dentiform ring-shaped edge and a pipeline on which a gasket is available for connecting the T-shaped pipe; in addition, an internal pipe is designed in the interior of the handle, whose both ends are connected to the T-shaped pipe and a rotiform joint respectively of the both ends of the handle. Moreover, on the rotiform joint, a silica gel tube is connected to the switching connector of the water pipe, so as to form a simple teeth cleaner.

3 Claims, 11 Drawing Sheets

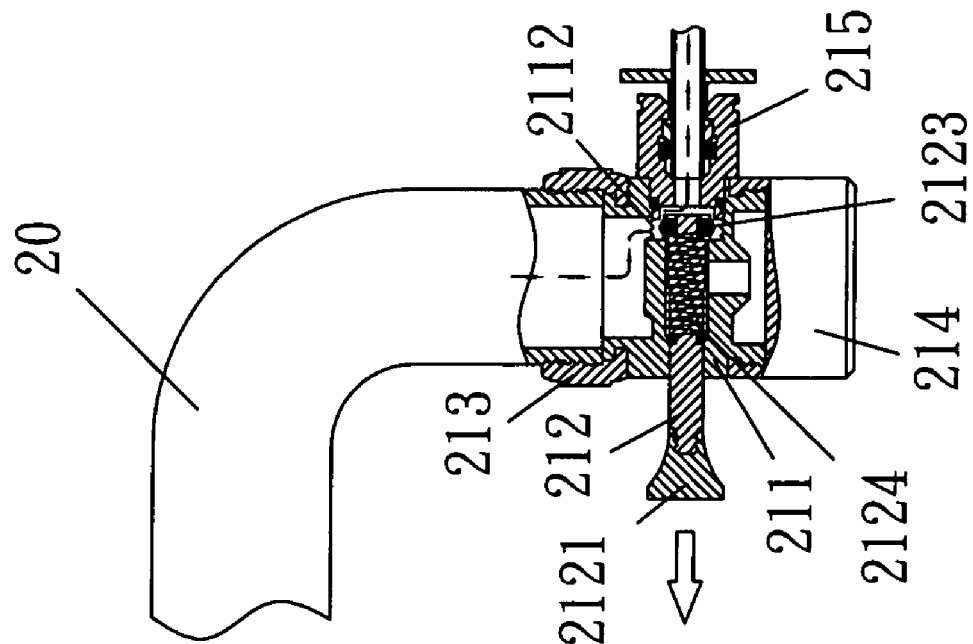
Fig.9-B
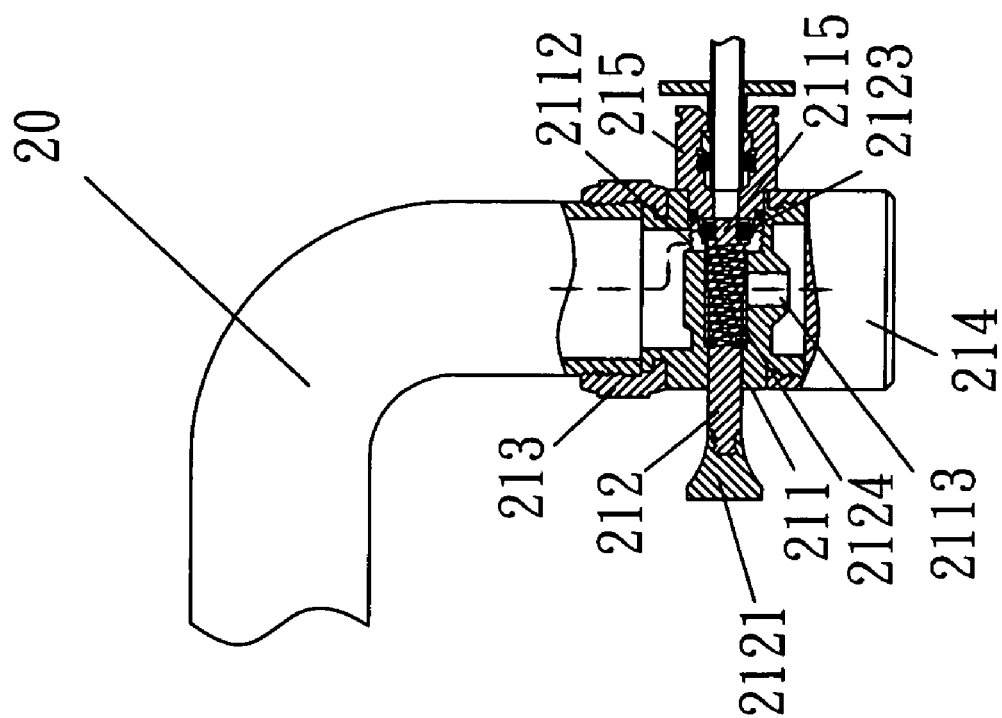
Fig.9-A

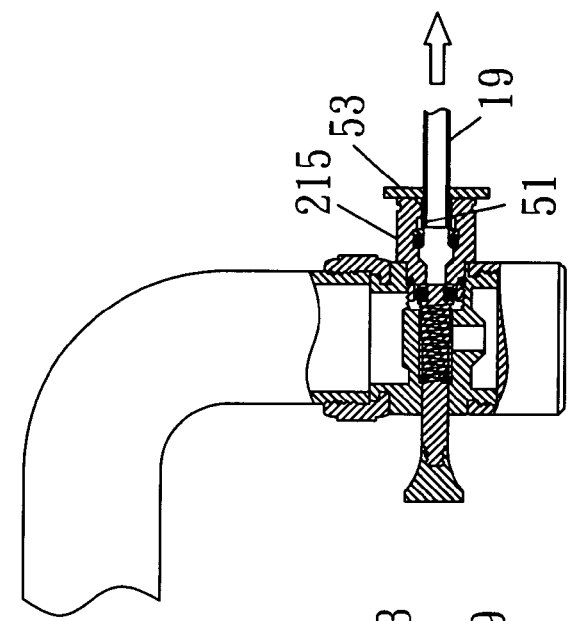
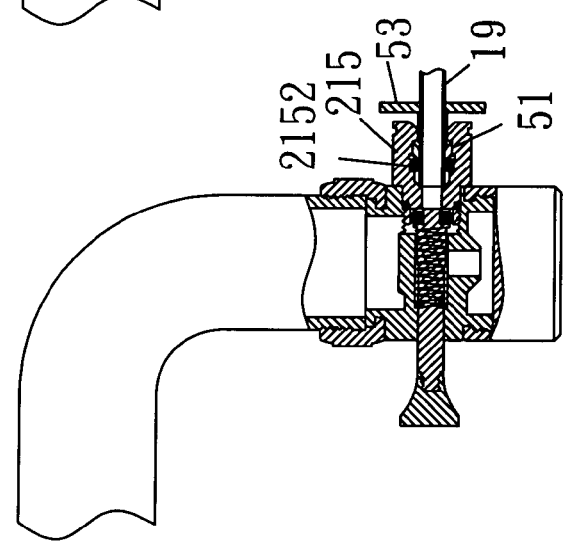
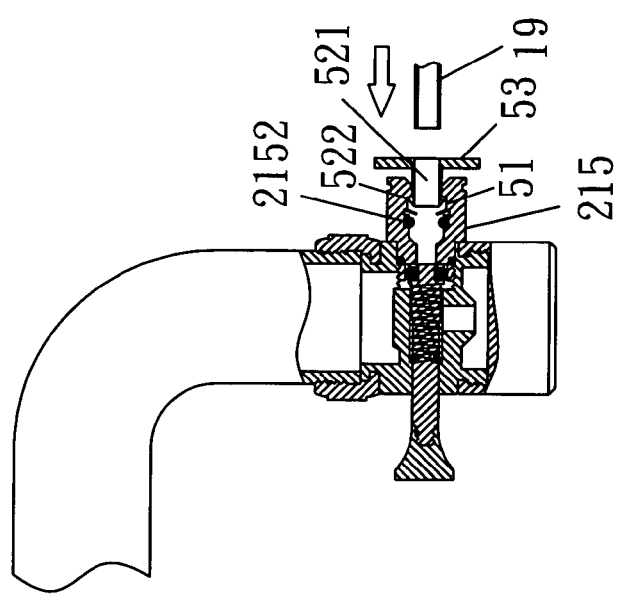
Fig.10-A  Fig.10-B  Fig.10-C

TEETH CLEANER

BACKGROUND OF THE INVENTION

1) Field of the Invention

The present invention relates to a kind of teeth cleaner, which is an improved one against the deficient structure of the prior art, more particularly, to a handy and improved teeth cleaner.

2) Description of the Prior Art

Generally, we will see a dentist is using a conventional teeth cleaner to rinse the teeth of a victim in a clinic to keep the teeth clean. However, this teeth cleaner is motor-type one, i.e. the foregoing functions can be realized based on being driven by a motor. The following defects should occur during use:

1. The sound of the motor during operation is too loud that makes the victim or user feel horrible and fretful.

2. If a single teeth cleaner were fixed for use, the squirt gun would fail to be alternated, resulting from unhygienic phenomena.

3. The teeth cleaner is expensive, so common people cannot bear that.

4. It fails to be popularized to the common family, because consumers cannot accept the price; and its weaken competitive edges do not accord with the production value and economic benefit.

SUMMARY OF THE INVENTION

In view of the foregoing defects, the inventor of the present invention eventually develops a kind of improved teeth cleaner after constantly research and development, which can solve the problems of the prior art. Therefore, the main purpose of the present invention is to provide an improved teeth cleaner, in which a squirt gun is designed at the front end of a handle, and a bending nozzle designed on the foremost position of the squirt gun while its end is designed to be as a dentiform ring-shaped edge and a pipeline on which a gasket is available for connecting the T-shaped pipe; in addition, an internal pipe is designed in the interior of the handle, whose both ends are connected to the T-shaped pipe and a rotiform joint respectively of the both ends of the handle. Moreover, on the rotiform joint, a silica gel tube is connected to the switching connector of the water pipe, so as to form a simple teeth cleaner.

BRIEF DESCRIPTION OF THE DRAWINGS

FIG. 9-A: the combination cutaway view of the switching joint under operation in accordance with the present invention.

FIG. 9-B: the combination cutaway view of the switching joint under operation in accordance with the present invention.

FIG. 10-A: the combination cutaway view of the switching joint under operation in accordance with the present invention.

FIG. 10-B: the combination cutaway view of the switching joint under operation in accordance with the present invention.

FIG. 10-C: the combination cutaway view of the switching joint under operation in accordance with the present invention.

DETAILED DESCRIPTION OF THE PREFERRED EMBODIMENTS

Figure 1:
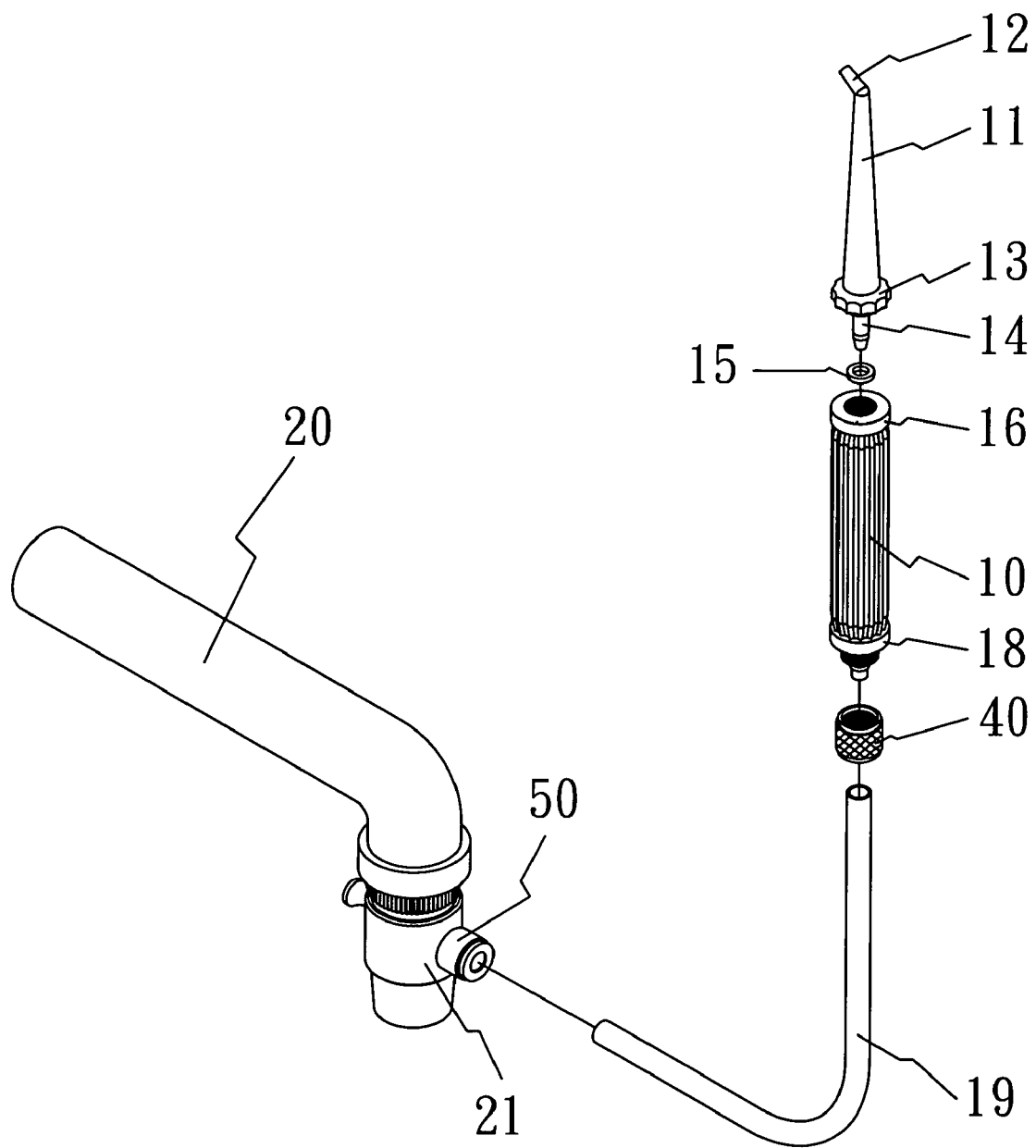
FIG. 1: the three-dimensional exploded view of the present invention.
Figure 2:
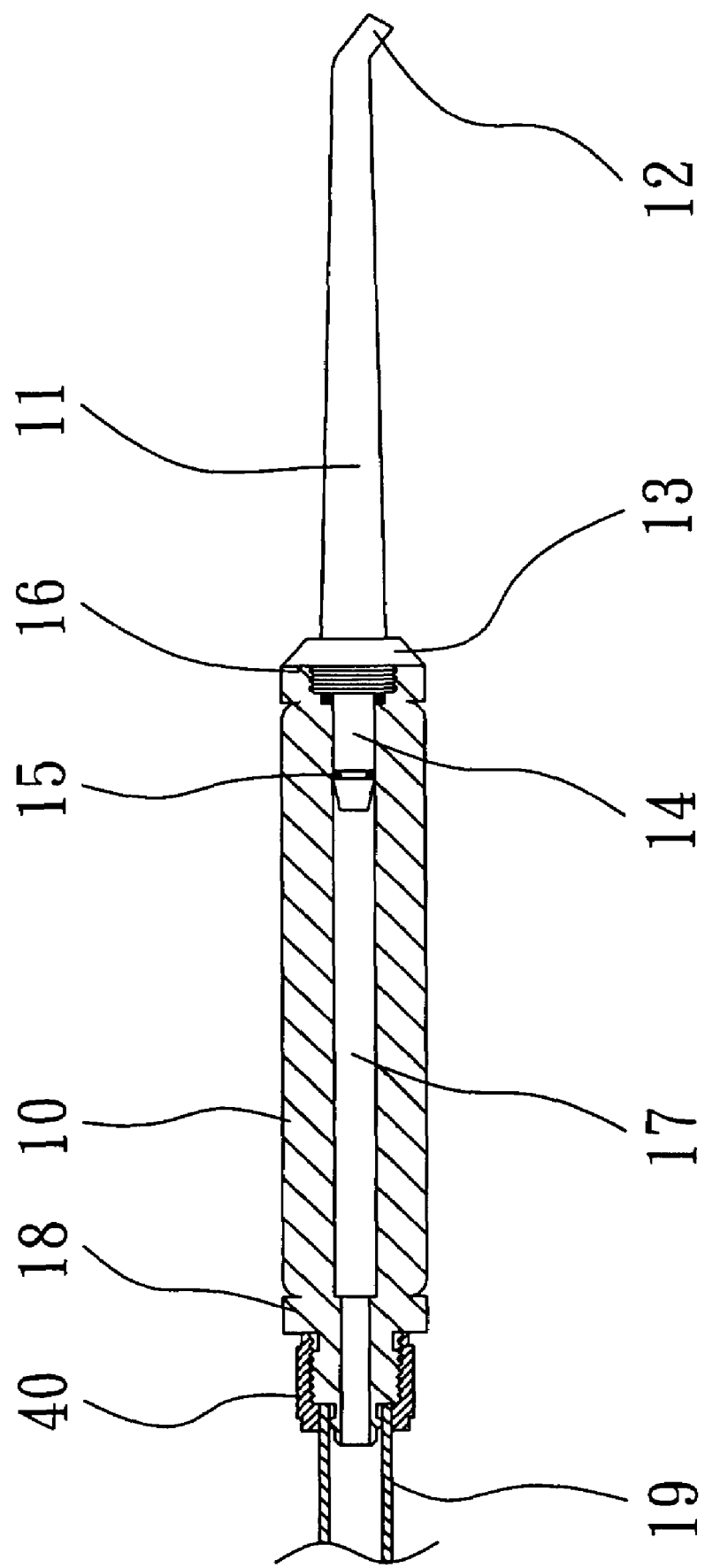
FIG. 2: the combination cutaway view of the present invention
Figure 6:
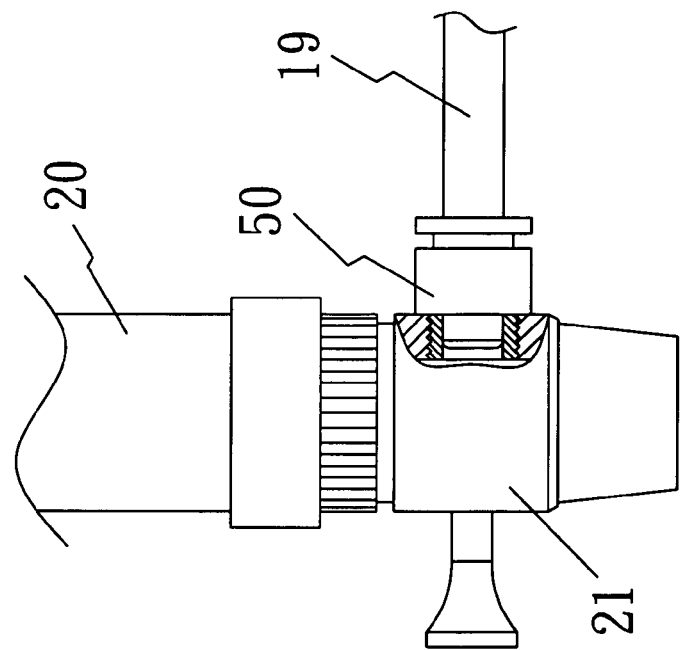
FIG. 6: the implementation sketch map of the present invention.
Figure 7:
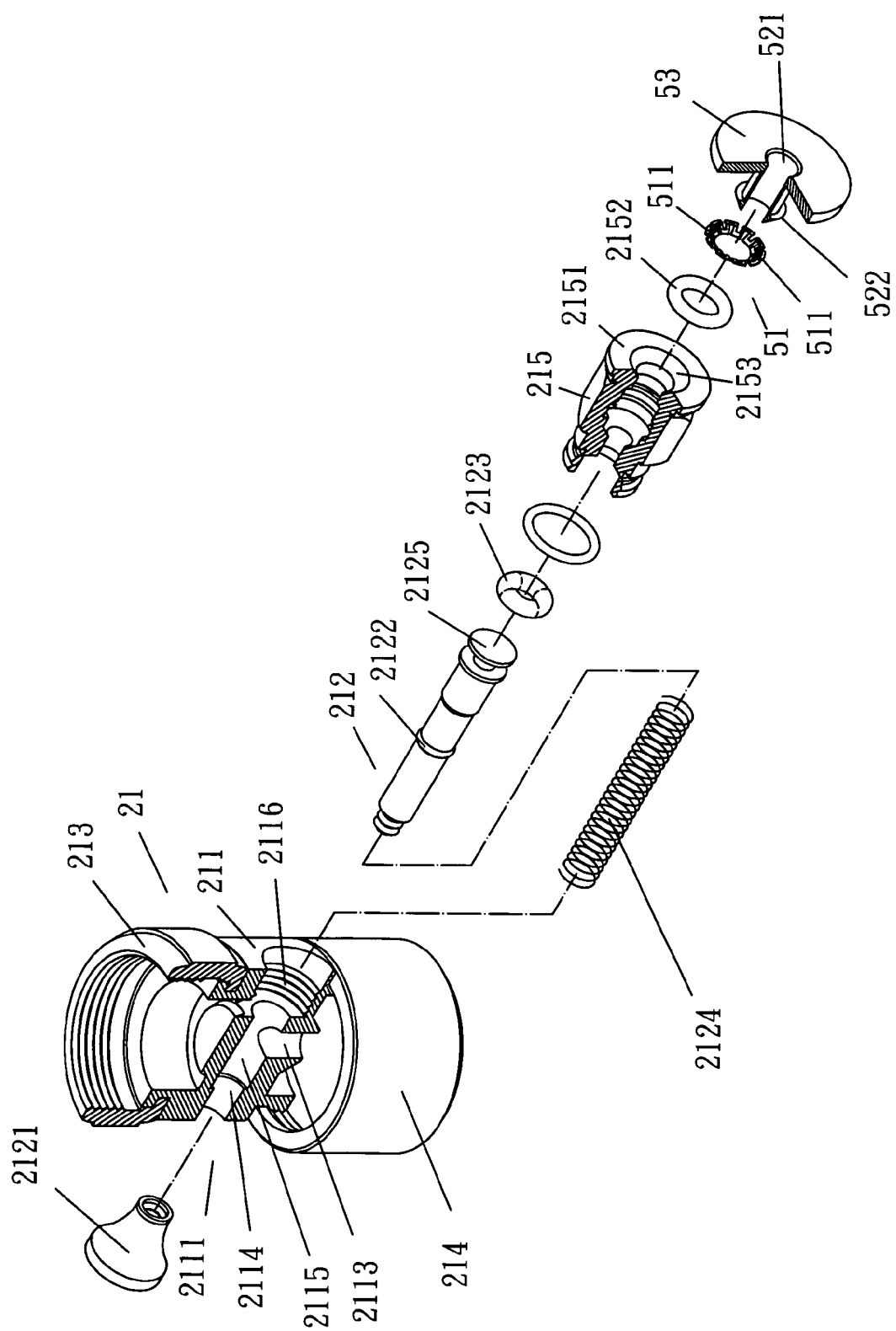
FIG. 7: the partial cutaway view of the switching joint in accordance with the present invention.
Figure 8:
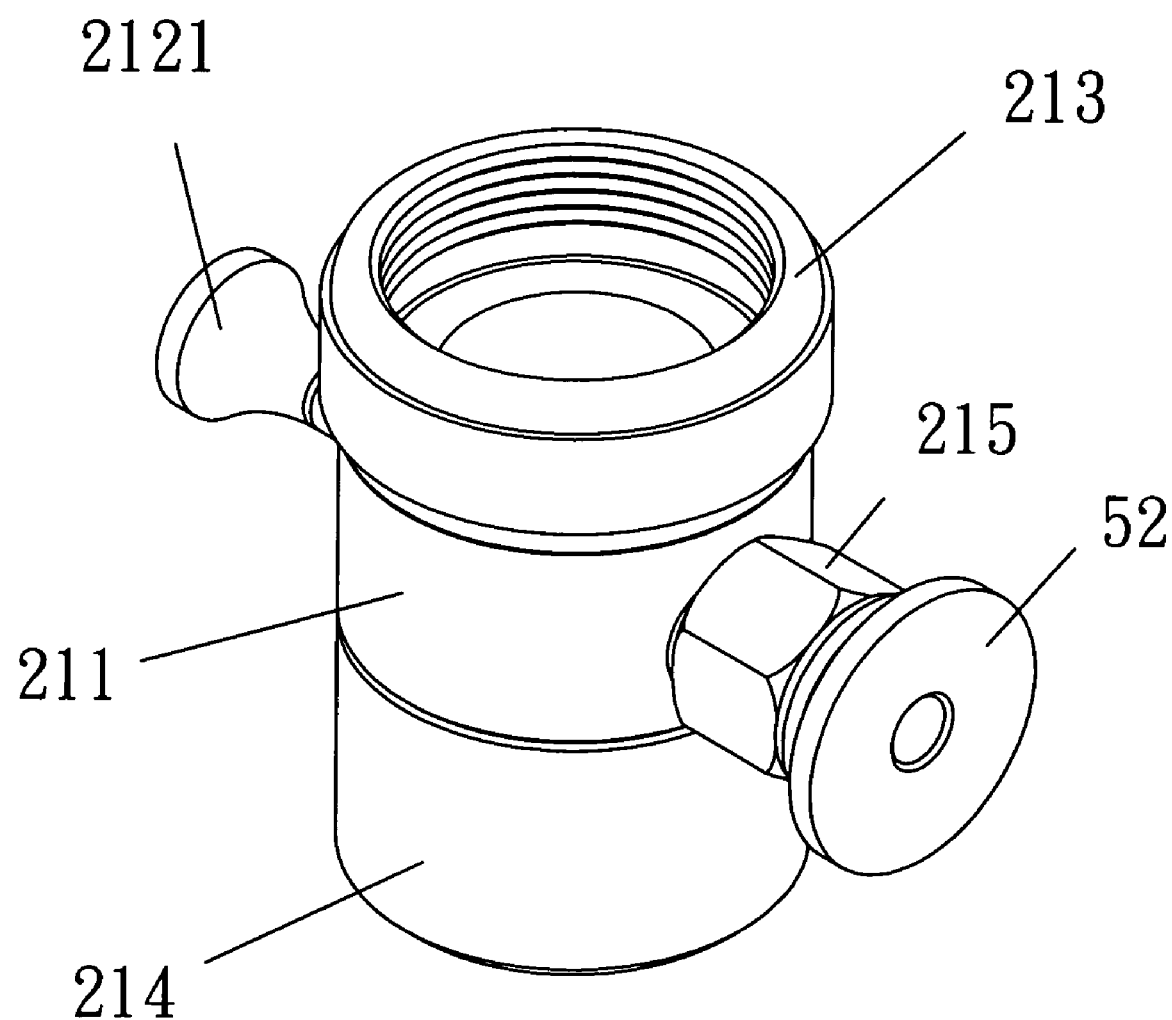
FIG. 8: the three-dimensional combination sketch map of the switching joint in accordance with the present invention.

Referring to FIG. 1 and FIG. 6, the present invention features:

To design a squirt gun 11 at the front end of a strip-run-shaped handle 10 on its surrounding surface, in which a bending nozzle 12 is designed on the foremost position of the squirt gun 11 to aim at the cleaned part while its end is designed to be as a dentiform ring-shaped edge 13 and a pipeline 14 on which a gasket 15 is available for connecting the T-shaped pipe 16; in addition, an internal pipe 17 is designed in the interior of the handle 10, whose both ends are connected to the T-shaped pipe 16 and a rotiform joint 18 respectively of the both ends of the handle. Moreover, on the rotiform joint, a silica gel tube 19 is connected to the switching connector 21 of the water pipe 20, so as to form a simple teeth cleaner. In which:

Referring to FIG. 7, FIG. 8, FIG. 9-A and FIG. 9-B, the switching connector 21 is composed of: interiorly a valve hole 2111 designed transversely, in which the top and end of the valve hole 2111 are designed a flow channel 2112 and 2113 respectively to connect to the valve pipe at the upper and lower sides and to be interlinked in the valve hole 2111; and a valve stem 212 with a pull knob 2121 is designed at its one end, a threading ring fixed at the upper side of the valve pipe 211, a water filter 214 fixed at the lower side of the valve pipe 211 and an bulged pipe 215. Make the valve hole 2111 in the interior valve pipe 211 be arranged with small, medium and big holes 2114, 2115, and 2116 in order from the end of pull knob 2121 of the valve stem 212, and make the flow channel 2112 at the top be at the big hole 2116, while the flow channel 2113 at the bottom is at the medium hole 2115. And middle section and foremost section of the valve stem 212 are interlinked with an O-ring seals 2122 and 2123, and a spring 2124 is interlinked with the middle section of the valve stem 212 from the big hole 2115 of the valve hole 211, and the pull knob is combined with the valve stem 212 from the small hole 2114 of the valve hole 211. Lastly, the bulged pipe 215 should be connected at the end of the big hole 2116 of the valve hole 211.

The teeth cleaner can be laid on a frame 30 fixed on the wall. The frame 30 is an inverse L-shaped sheet, whose wall side 31 is designed with a perforation 311, so that the fixing unit 312 can be screwed into the wall for fixing. And at the central bottom, a round base 313 is available for the placement of the handle 10; in addition, some equidistant slots 321 are set on the vertical sheet 32 and a recess 322 is designed at the semicircular base 313 the center is corresponding to, for the placement of the spurt gun and the teeth cleaner.

Figure 12:
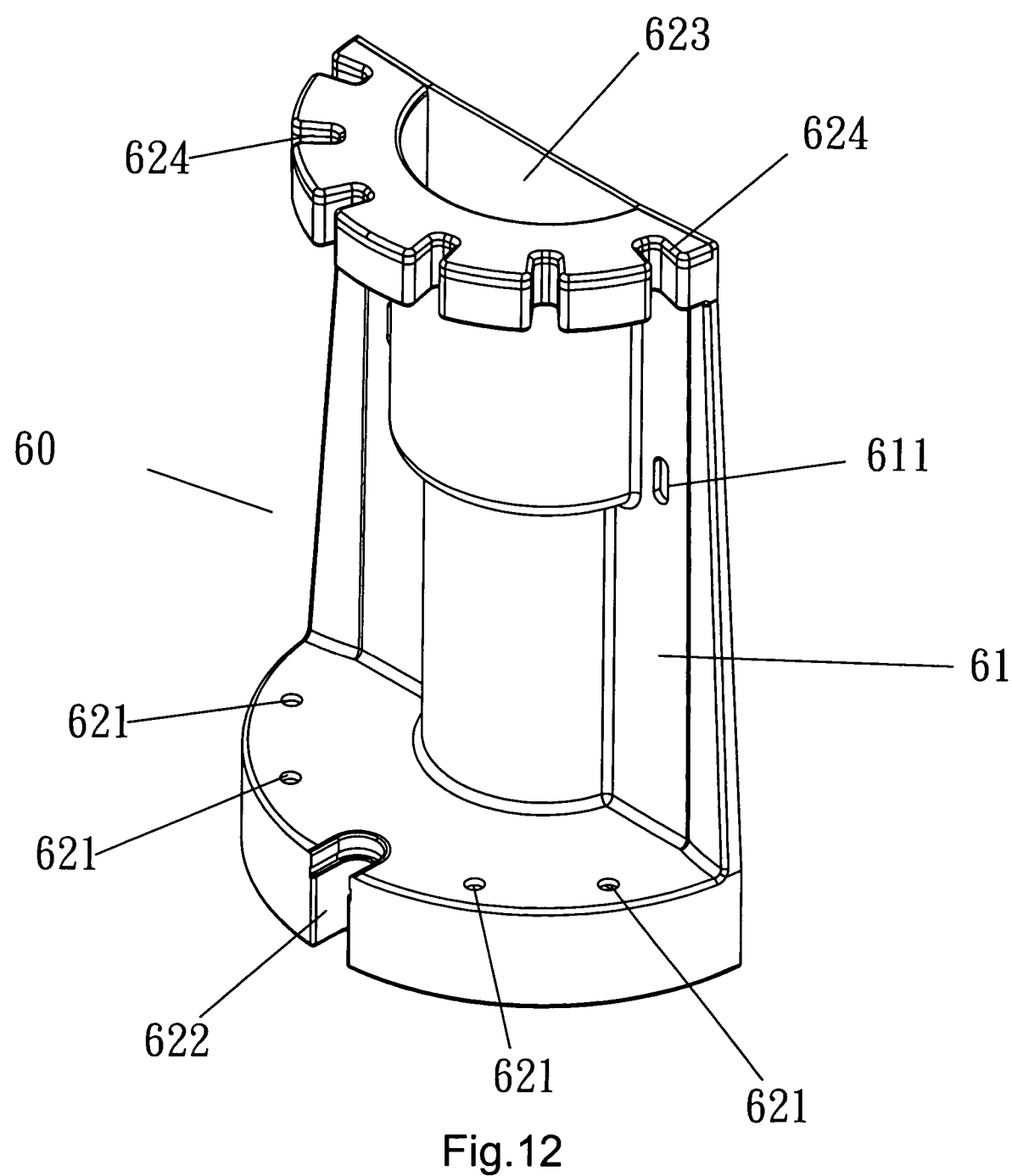
FIG. 12: the three-dimensional appearance view of another embodiment of the frame in accordance with the present invention.

As shown in FIG. 12, the frame 60 fixed on the wall for the replacement of the teeth cleaner can be a semicircular one with upper and lower layers. Its wall side has perforation 611, so that the fixing unit can be screwed into the wall for fixing; and its lower layer has many equidistant slots 621 for the insertion of the spurt gun 11, while the center has a recess 622 for the replacement of the teeth cleaner; and at the center of the upper layer, a recess 623 is available for the teeth cleaner, besides some equidistant recesses 624 designed at the outer edge.

The both ends of the silica gel tube 19 are connected and fixed by an empaistic ring 40 and quick coupler 50. So it can be assembled or disassembled easily.

Referring to FIG. 7, FIG. 8, FIG. 10-A, FIG. 10-B and FIG. 10-C, the quick coupler 50 interlinked in the position groove 2153 of the internal locking ring 2152 of the water outlet 2151 of the bulged pipe 215 of the switching connector 21 comprises: an elastic locking ring 51 whose internal peripheral ring has many locking sheets 511, and a locking base 53 whose center is designed as a pipeline 521, and the end of the pipeline has a ring-shaped pushing edge 522.

Referring to FIG. 1-FIG. 6, as far as the assembly of the present invention concerned, the handle 10 is put into the internal pipe 17 firstly, and its both ends are connected to the T-shaped pipe 16 and spurt gun 11, and rotiform joint respectively, so that the empaistic ring 40 can lock the silica gel pipe 19. And the another end of the silica gel pipe 19 is interlinked on the switching connector 21 of the water pipe 20 with a quick coupler 50, further to form a whole one. Therefore, the smooth and convenient operation can be realized.

Figure 3:
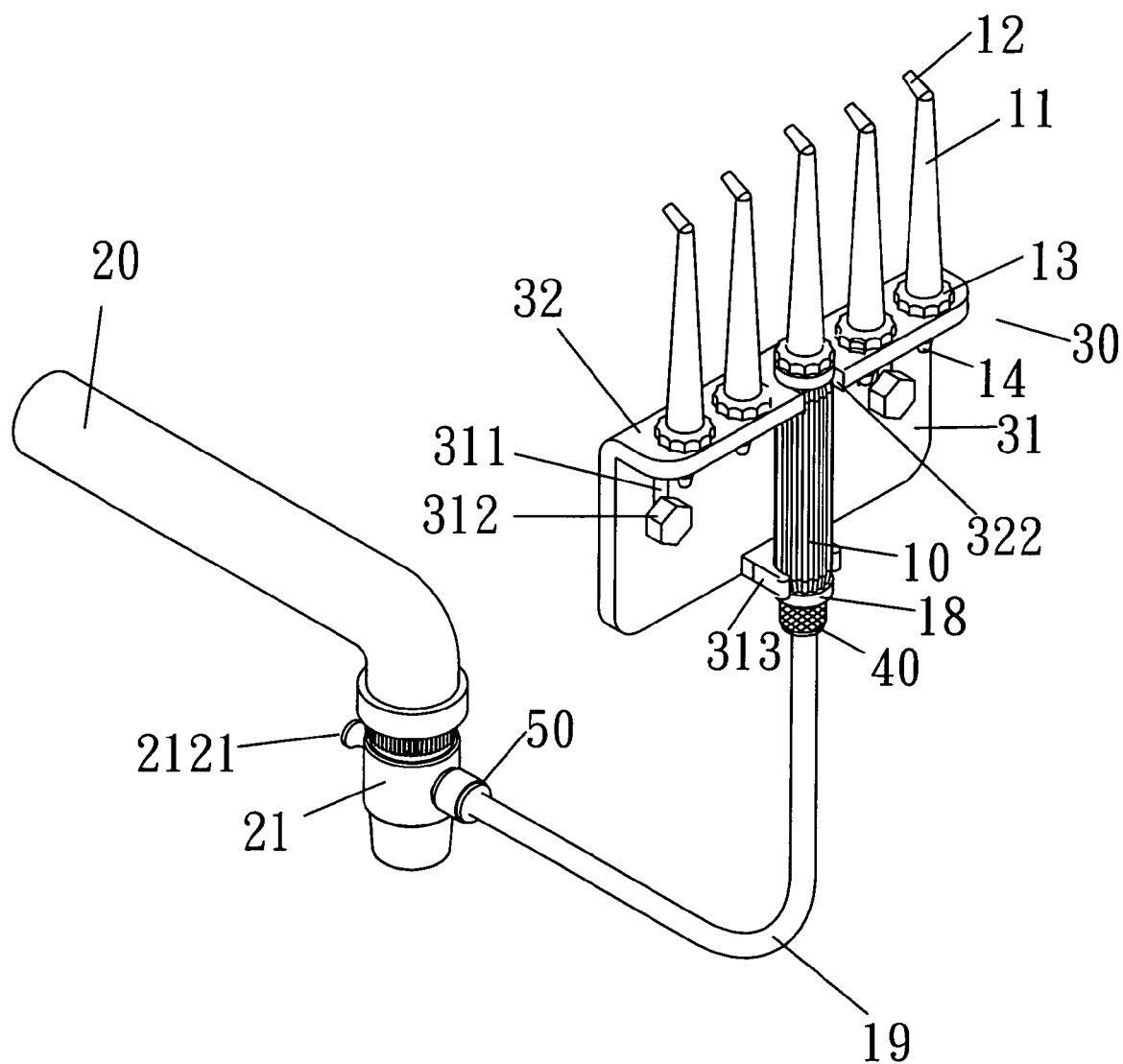
FIG. 3: the sketch map of the present invention under implementation.
Figure 4:
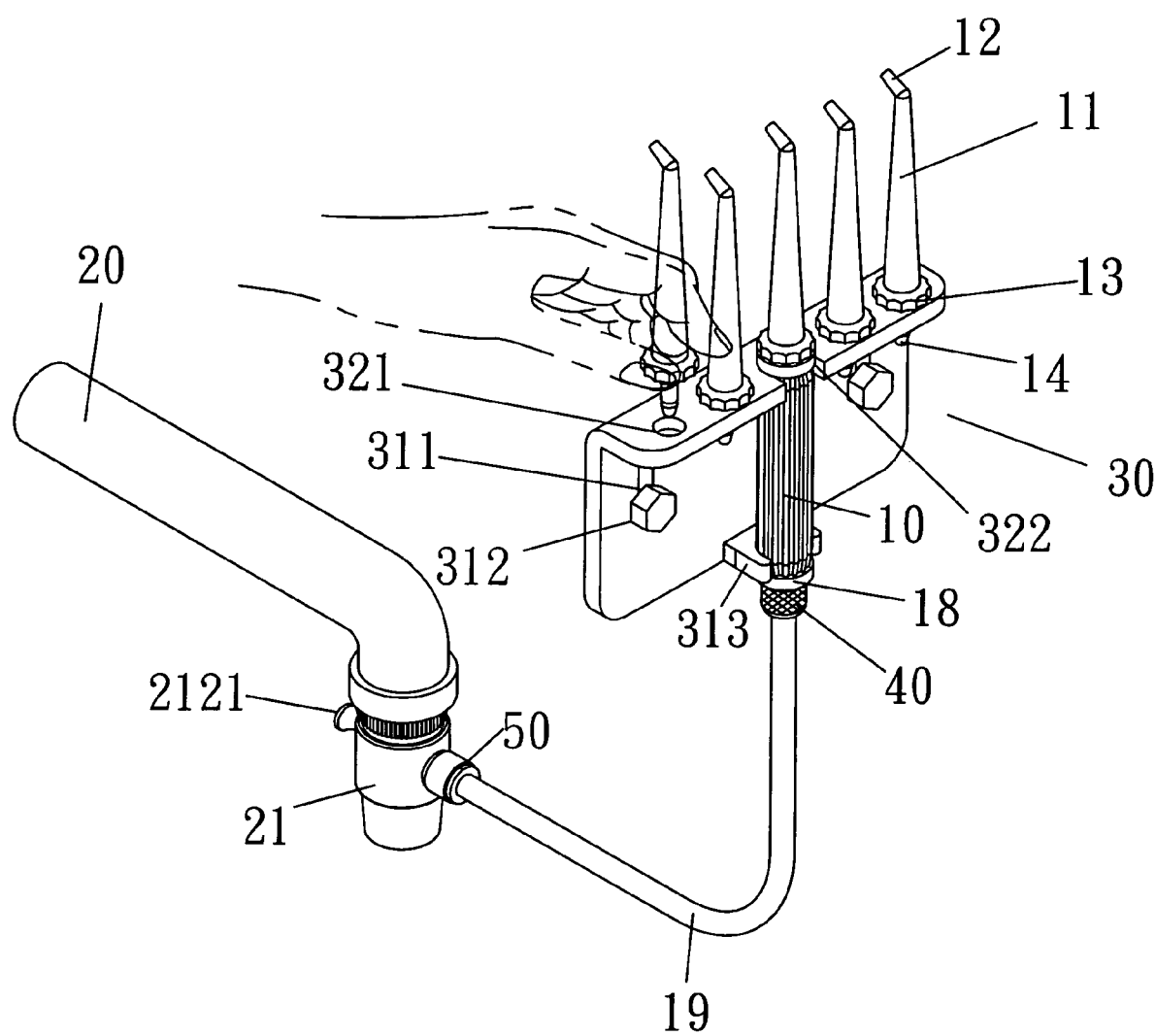
FIG. 4: the sketch map while acting in accordance with the present invention.

In addition, while using the teeth cleaner, as shown in FIG. 3, the whole set of teeth cleaners and single spurt gun 11 can be placed on the frame 30, which is fixed on the wall with a fixing unit 312, so that the user can select his/her own spurt gun 11 and assemble it on the teeth cleaner to rinse the teeth (as shown in FIG. 4).

The spurt gun 11 of the present invention can be designed in various colors, so that the member of a family can distinguish their own spurt gun 11, meeting the personal sanitation requirement; the spurt gun 11 can be placed or taken conveniently, because it is cone-shaped. And the dentiform ring-shaped edge 13 at its end should be placed in the slots 321 of the frame 30 for stable fixing; The whole set of teeth cleaner the present invention provides can be taken or placed easily while being placed in the recess 322 and semicircular base 313 of the frame. The spurt gun 11 can be separated from the handle 10 and replaced easily by only averting the dentiform ring-shaped edge 13, and then by interlinking the spurt gun with the threading ring.

Because each spurt gun 11 is detachable from the handle 10, we can buy the teeth cleaner by selecting the single handle arranged with the quantity of required spurt guns 11. After using for some time, the spurt gun 11 can be discarded and replaced.

Therefore, the improved teeth cleaner can be installed in hotels and restaurants etc. And owners can provide a handle and spurt guns with required quantity in each room without much additional cost, so as to replace the used ones after guests' leaving and obtain good service quality and sanitation effect.

Moreover, when user takes the teeth cleaner to rinse his/her teeth, user can pull outwards the pull knob 2121 of the switching connector 21 connected to the water pipe 20 to make valve stem overcome the elasticity of the spring 2124, the foremost end 2125 and O-ring seal 2123 at foremost section will hold the junction of the big hole 2116 and medium hole 2115 of the valve hole 211 to make the water flow by the interior of threading ring 213 of the switching joint 21, by top flow channel 2112 of the valve hole 2111 of the valve pipe 211, and by big and medium hole 2116, 2115 of the valve hole 2111, and by the internal joint of the bulged pipe 215 and valve hole 2111 and to the interior of the bulged pipe 215, lastly, by the spurt gun 11 through the silica gel tube 19, and would be sprayed by the nozzle 12 towards the cleaned teeth; contrarily, on the occasion of nonuse, just to shut off the water or push the pull knob 2121 of switching joint inwards to make the spring 2124 interlinked at the middle section of the valve stem 212 push the valve stem 212 onwards actively with its elasticity, and the foremost edge 2125 of the valve stem 212 and 0-ring seal 2123 at the foremost section can hold the internal junction of the bulged pipe 215 and valve hole 2111 tightly. Lastly replace the teeth cleaner on the frame.

Figure 5:
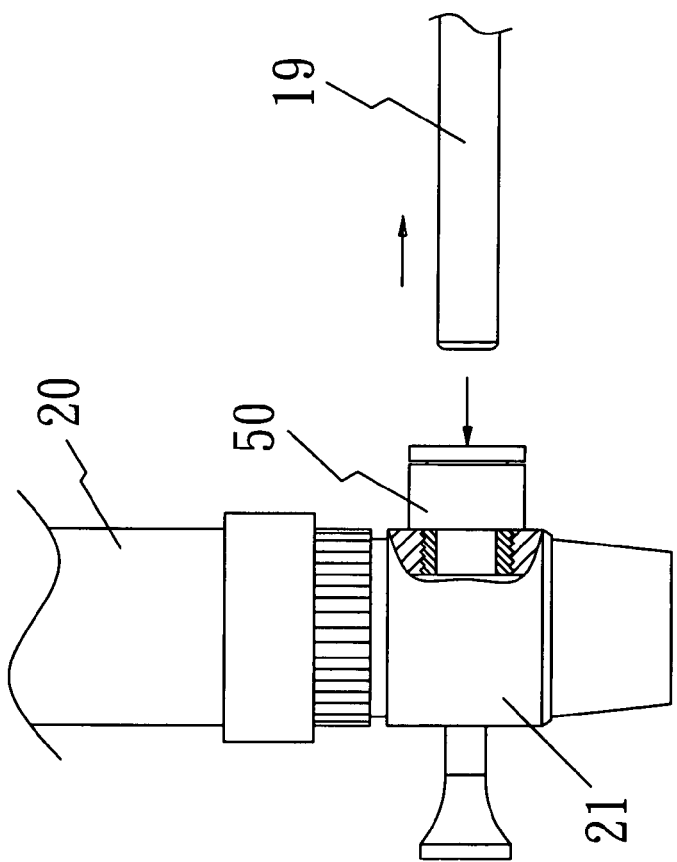
FIG. 5: the implementation sketch map of the present invention.

And, the switching joint on the silica gel tube 19 and the water pipe 20 is fixed with a quick coupler 50 to make the silica gel tube 19 directly can be interlinked from the pipeline 521 at the center of the locking base 53 (as shown in FIG. 10-A), when the water outlet 2151 of the bulged pipe 215 20 is combined with the silica gel tube 19, by the locking sheet 511 designed at the internal peripheral ring within the elastic locking ring 51, lastly, by the locking ring 2152. Based on the action of the locking sheet 511, the silica tube 19 can be integrated with the bulged tube 215 by means of locking (as shown in FIG. 10-B); While separating the silica gel tube 19 from the bulged pipe 215, the locking base 53 can pushed towards the bulged pipe 215 to make the ring-shaped pushing edge 522 at the end of pipeline 521 push the locking sheet 511 designed at the internal peripheral ring within the elastic locking ring 51 outwards, so as to make the silica gel tube 19 no longer be locked by the locking sheets 511; lastly to take the silica gel tube 19 out. Therefore the teeth cleaner not only can be assembled or disassembled easily, but also its service life can be extended (as shown in FIG. 5, FIG. 6, FIG. 10-A, FIG. 10-B and FIG. 10-C).

Figure 11:
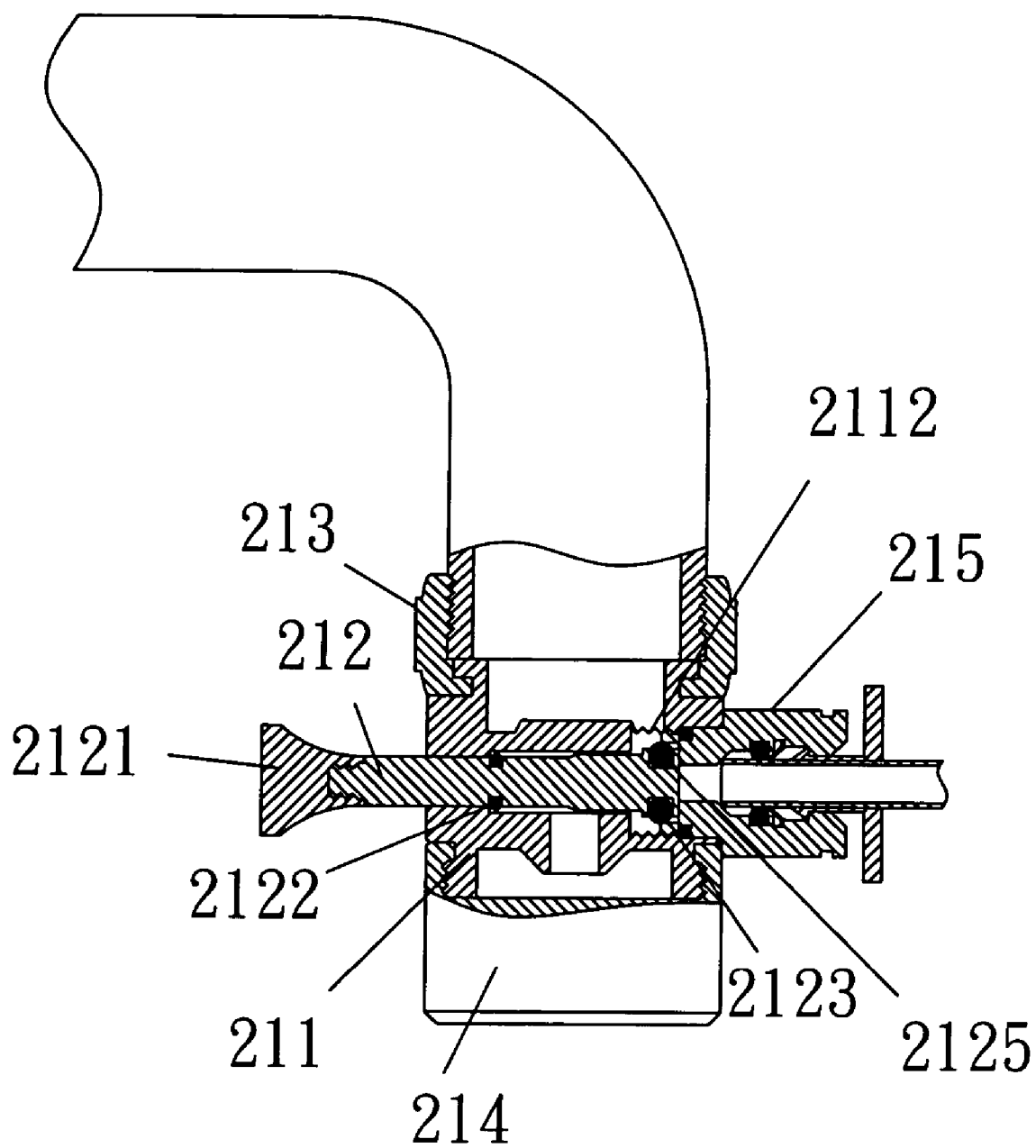
FIG. 11: the combination cutaway view of another embodiment of the switching joint in accordance with the present invention.

Besides, as shown in FIG. 11, the middle section of the valve stem 212 can not be interlinked with any other spring 2124, so that we can further select and control output or switch of the bulged pipe 215 or water filter 214 manually when the water accesses to the interior of the switching joint 21.

And, the water pipe connected with the switching joint 21 can be equipped with a one way faucet with single cool water outlet or combination faucet with cool and warm water outlets to make the water temperature from the teeth cleaner can be adjusted to the required one (such as teeth's sensibility to cool or living in frigid zone). Thus it can be used widely.

What is claimed is:

1. An improved teeth cleaner, comprising:
a squirt gun including: a handle; a bending nozzle at one end of the handle having a ring-shaped edge and a gasket for connecting a T-shaped pipe; and a joint at the opposite end of the handle having a ring abutting the joint; wherein an internal pipe runs through the interior of the handle, one end of the interior pipe being connected to the T-shaped pipe and another end being connected to the joint and the ring being selectively attached to one end of a flexible hose; and
a switching connector selectively connected to an opposite end of the flexible hose, the switching connector including: a valve hole running transversely through the switching connector, in which the valve hole includes an upper flow channel fluidly connected to a valve pipe above the valve hole, and a lower flow channel fluidly connected with a water filter fixed at a lower side of the valve pipe; a threading ring fixed at the upper side of the valve pipe; a valve stem having a spring-loaded pull knob is located at one end of the valve hole; and a bulged pipe connected to the opposite end of the valve hole.

2. The teeth cleaner, as recited in claim 1, further comprising a quick coupler interlinked in a position groove of an internal locking ring of a water outlet of the bulged pipe of the switching connector.

3. The teeth cleaner, as recited in claim 1, wherein the switching connector further comprises:
small, medium and big holes in the valve hole arranged in order from the pull knob of the valve stem, the upper flow channel being located at the big hole, the lower flow channel being located at the medium hole;
wherein the valve stem having a middle section and a foremost section, each section interlinked with an O-ring seal; and
a spring interlinked with the middle section of the valve stem adjacent the big hole, wherein the spring-loaded pull knob is linked with the valve stem adjacent the small hole of the valve hole, and wherein the bulged pipe is connected to the big hole of the valve hole.

* * * * *